(12) United States Patent
Weber et al.

(10) Patent No.: US 7,491,225 B2
(45) Date of Patent: Feb. 17, 2009

(54) SYSTEM AND METHOD FOR DEPLOYING A DRUG-ELUTING EXTERNAL BODY AND TISSUE SCAFFOLD

(75) Inventors: Jan Weber, Maple Grove, MN (US); Brian J. Brown, Hanover, MN (US); Richard C. Gunderson, Maple Grove, MN (US); Susan Shoemaker, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 317 days.

(21) Appl. No.: 11/059,242

(22) Filed: Feb. 16, 2005

(65) Prior Publication Data
US 2006/0184237 A1    Aug. 17, 2006

(51) Int. Cl.
*A61F 2/06* (2006.01)
(52) U.S. Cl. ...................................... 623/1.11
(58) Field of Classification Search ....... 623/1.11–1.13, 623/1.23
See application file for complete search history.

(56) References Cited

U.S. PATENT DOCUMENTS

| | | | |
|---|---|---|---|
| 4,655,771 A | 4/1987 | Wallsten | |
| 4,954,126 A | 9/1990 | Wallsten | |
| 5,824,049 A | 10/1998 | Ragheb et al. | |
| 5,954,764 A * | 9/1999 | Parodi | 623/1.11 |
| 6,096,070 A | 8/2000 | Ragheb et al. | |
| 2002/0045931 A1 * | 4/2002 | Sogard et al. | 623/1.13 |
| 2003/0153968 A1 | 8/2003 | Geis et al. | |
| 2003/0236567 A1 * | 12/2003 | Elliot | 623/1.13 |
| 2004/0215213 A1 | 10/2004 | Dolan | |
| 2004/0236403 A1 * | 11/2004 | Leonhardt et al. | 623/1.13 |

FOREIGN PATENT DOCUMENTS

WO    WO 00/32137 A    6/2000

OTHER PUBLICATIONS

Yoseph Bar-Cohen, "Electro-active polymers: current capabilities and challenges", Paper 4695-02, *Proceedings of the SPIE Smart Structures and Materials Symposium EAPAD Conference*, San Diego, CA, Mar. 18-21, 2002.

* cited by examiner

*Primary Examiner*—Todd E Manahan
*Assistant Examiner*—Ryan Severson
(74) *Attorney, Agent, or Firm*—Kenyon & Kenyon LLP

(57) ABSTRACT

A medical appliance is provided that includes a self-expanding stent; a sheath adapted to enclose the self-expanding stent in an interior space during deployment; and an external body comprising a bioactive agent attached to the self-expanding stent and adapted to lie outside the interior space of the sheath when the self-expanding stent is enclosed in the sheath. The medical appliance may be deployed in a lumen of a human body and the external body may release the bioactive agent. A method of producing a medical device is provided that includes attaching an external body to a stent and coupling the stent to a delivery arrangement. The external body includes a bioactive agent. A medical device is provided that includes a tissue scaffold; a sheath adapted to enclose the tissue scaffold in an interior space during deployment; and an external body comprising endothelial cells attached to the tissue scaffold and adapted to lie outside the interior space of the sheath when the tissue scaffold is enclosed in the sheath.

22 Claims, 10 Drawing Sheets

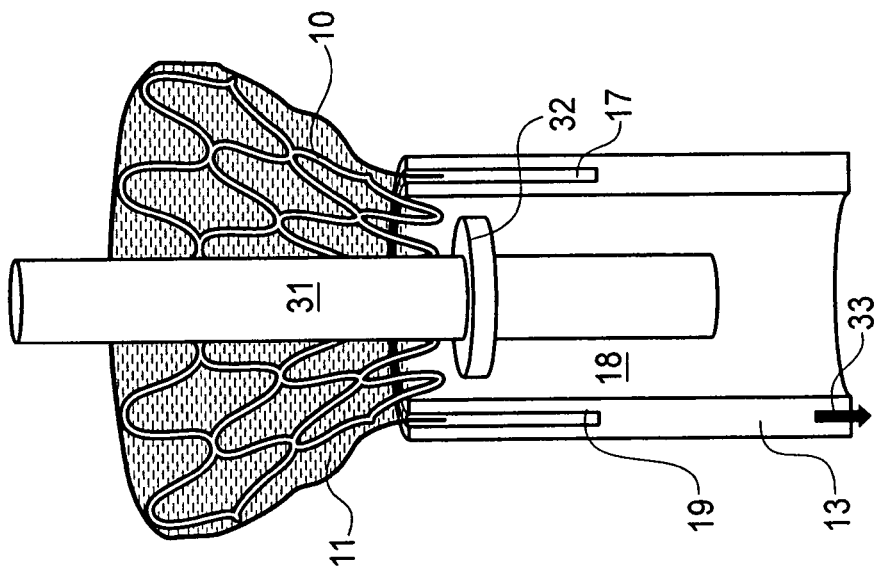
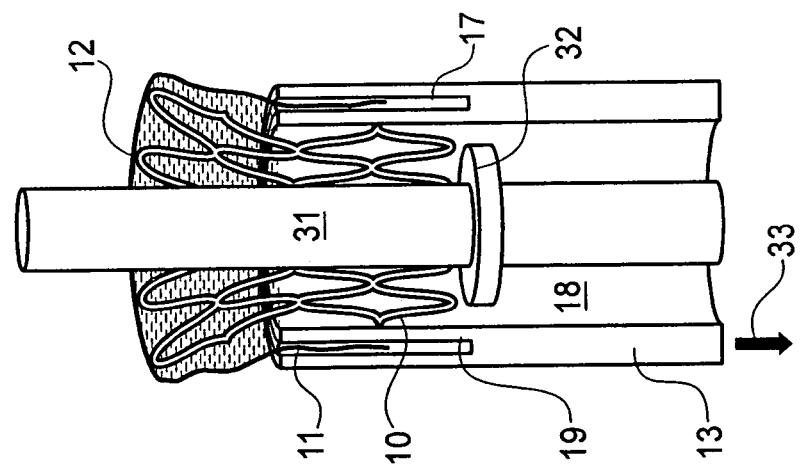
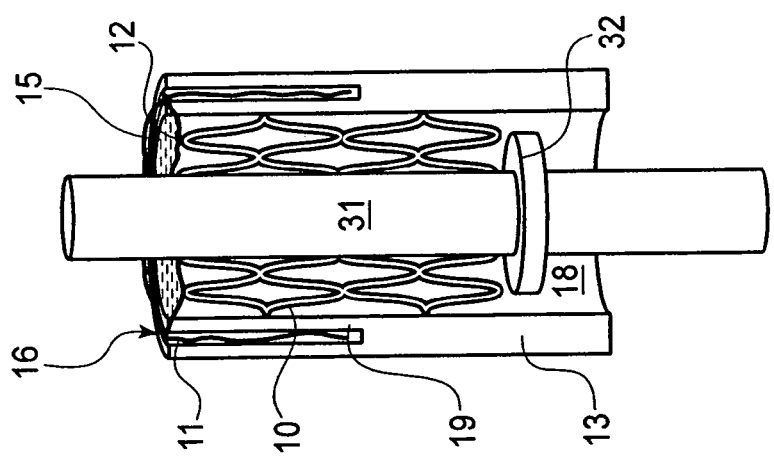

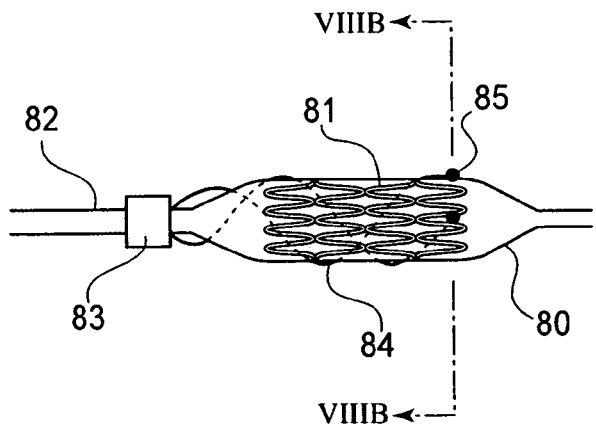
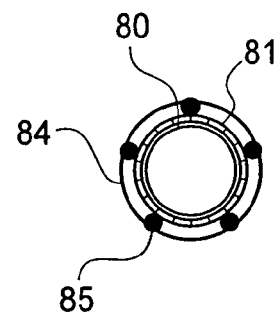
FIGURE 8A
FIGURE 8B
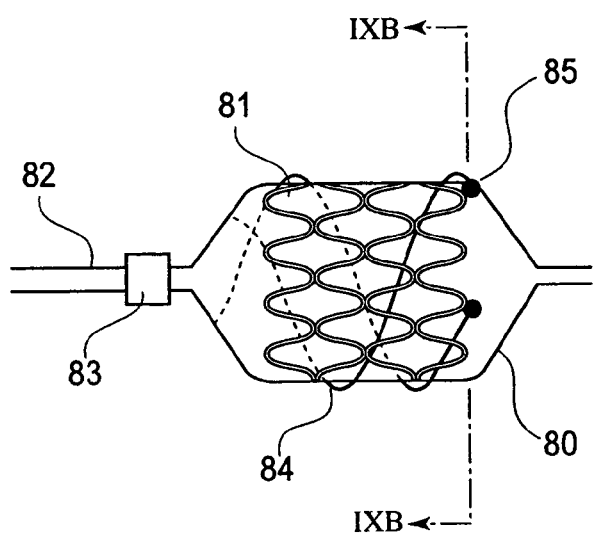
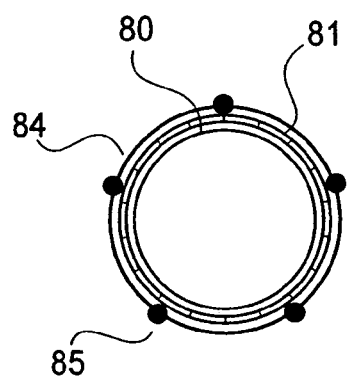
FIGURE 9A
FIGURE 9B

SYSTEM AND METHOD FOR DEPLOYING A DRUG-ELUTING EXTERNAL BODY AND TISSUE SCAFFOLD

FIELD OF THE INVENTION

The present invention relates to medical appliances. More particularly, the present invention relates to drug-eluting external bodies and a method of incorporating a drug-eluting external body in a medical device.

BACKGROUND INFORMATION

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with the therapeutic agent to be locally delivered. The coating on medical devices may provide for controlled release, which may include long-term or sustained release, of a bioactive material.

Aside from facilitating localized drug delivery, medical devices may be coated with materials to provide beneficial surface properties. For example, medical devices are often coated with radiopaque materials to allow for fluoroscopic visualization while placed in the body. It is also useful to coat certain devices to achieve enhanced biocompatibility and to improve surface properties such as lubriciousness.

Coatings have been applied to medical devices by processes such as dipping, spraying, vapor deposition, plasma polymerization, spin-coating and electrodeposition. Although these processes have been used to produce satisfactory coatings, they have numerous, associated potential drawbacks. For example, it may be difficult to achieve coatings of uniform thicknesses, both on individual parts and on batches of parts. Further, many conventional processes require multiple coating steps or stages for the application of a second coating material, or may require drying between coating steps or after the final coating step.

The spray-coating method has been used because of its excellent features, e.g., good efficiency and control over the amount or thickness of coating. However, conventional spray-coating methods, which may be implemented with a device such as an airbrush, have drawbacks. For example, when a medical device has a structure such that a portion of the device obstructs sprayed droplets from reaching another portion of the device, then the coating becomes uneven. Specifically, when a spray-coating is employed to coat a stent having a tube-like structure with openings, such as stents described in U.S. Pat. Nos. 4,655,771 and 4,954,126 to Wallsten, the coating on the inner wall of the tube-like structure may tend to be thinner than that applied to the outer wall of the tube-like structure. Hence, conventional spraying methods may tend to produce coated stents with coatings that are not uniform. Furthermore, conventional spraying methods are inefficient. In particular, generally only 5% of the coating solution that is sprayed to coat the medical device is actually deposited on the surface of the medical device. The majority of the sprayed coating solution may therefore be wasted.

In the spin-dipping process, a medical device is coupled to a spinning device, and then, while rotating about a central axis, the medical device is dipped into a coating solution to achieve the desired coating. This process also suffers from many inefficiencies including the unevenness of the coated layer and a lack of control over the coated layer's thickness.

In addition to the spray coating and spin-dipping methods, the electrostatic deposition method has been suggested for coating medical devices. For example, U.S. Pat. Nos. 5,824,049 and 6,096,070 to Ragheb et al. mention the use of electrostatic deposition to coat a medical device with a bioactive material. In the conventional electrodeposition or electrostatic spraying method, a surface of the medical device is electrically grounded and a gas may be used to atomize the coating solution into droplets. The droplets are then electrically charged using, for example, corona discharge, i.e., the atomized droplets are electrically charged by passing through a corona field. Since the droplets are charged, when they are applied to the surface of the medical device, they will be attracted to the surface since it is grounded.

One disadvantage of conventional electrostatic spraying is that it requires a complicated spraying apparatus. In addition, because conventional electrostatic systems use a gas to move the droplets from a source to a target, controlling the gas pressure is crucial for accurate coating. However, it is not easy to control the gas pressure so that the target surface is evenly and sufficiently coated without losing much of the coating solution.

Another method of coating a device can be achieved with electrohydrodynamic spraying. Using this method, a gas is not needed to disperse the coating. Electrohydrodynamic coating is accomplished by forcing a compatible solution through a nozzle assembly that has been electrically charged. The coating solution passes through the charged nozzle where it is electrically charged. As the solution exits the nozzle, the solution atomizes as the charged particles repel each other. This action forms the spray mist. The charged particles are attracted to the device to be coated when the device is connected to an electrical ground.

Devices may be coated by a gas assisted spraying process. A polymer/drug combination may be dissolved in a solvent mixture. The solution may be sprayed onto the devices and a polymer/drug film may be formed when the solvents evaporate. The ability to apply thin coatings on products may be limited by the capabilities of a gas assisted spraying process. The coating may flow on the medical device prior to drying, thereby creating an uneven concentration of bioactive agent on the surface of the device. A gas assisted spraying process may have a high variability for thin coatings.

Conventional methods of coating stents or devices with a drug-polymer layer, such as spraying or dipping, may require a solution of the drug-polymer to physically wet the surface of the stent. Spraying or dipping may cause uneven and unpredictable wetting, and distribution and evaporation of the solvent molecules may result in a non-uniform coating. The drying of the coating may lead to cracking and/or points of stress in the coating. A non-uniform coating may lead to the unit failing agent release requirements, drug uniformity and coating thickness specifications.

During deployment and loading of self-expanding (SE) stents, there may be significant friction between the stent surface and the sheath. Longer stents may have higher friction forces. These shear forces may be especially damaging in relation to coated SE stents. As the application of drug eluting coatings allows the use of longer stents, the problems resulting from this frictional interaction may increase. Similarly, during deployment of balloon-expandable stents, there may be a significant friction between the unfolding balloon and the stent surface.

Additionally, due to the large weight of a stent in relation to a coating weight (with SIBS\paclitaxel coating weight to stent weight having a ratio of approximately 1 to 1000), it may be difficult to measure the exact amount of drug coating on a stent.

Furthermore, due to the complex shape of a stent, it may be difficult to produce a homogeneous uniform coating on the stent surface. Similarly, the deposition of a drug coating that has a predefined pattern over the stent surface (for example, a 20% increased drug concentration at both ends of the stent in order to anticipate edge effects) may be difficult.

There is, therefore, a need for a cost-effective method of linking drug release coatings to the medical device which is not sensitive to the loading and deployment forces. The method should assure defect-free coatings and uniform drug dose per unit device. The method would provide better control of the agent release profile of the device, including increasing or decreasing the release of the bioactive agent. The method would also improve the quality of the coating of the device by allowing drug concentration variations as well as different drugs on different parts of the device. The method would thus allow for better control of the sensitivity of the bioactive material and would reduce variations in the coating properties. Each of the references cited herein is incorporated by reference herein for background information.

SUMMARY

A medical appliance is provided that includes a self-expanding stent; a sheath adapted to enclose the self-expanding stent in an interior space during deployment; and an external body comprising a bioactive agent attached to the self-expanding stent and adapted to lie outside the interior space of the sheath when the self-expanding stent is enclosed in the sheath.

The external body may be attached to a distal end of the self-expanding stent. The external body may be a membrane. The membrane may reside in an annular space in the sheath outside of the interior space when the self-expanding stent is enclosed in the interior space. The annular space in the sheath may be defined by an outer protective tube situated on an exterior of the sheath. Deploying the self-expanding stent may cause the membrane to be extracted from the annular space. The membrane may be impermeable to a fluid. The bioactive agent may include endothelial cells. The membrane may be porous to a fluid.

The external body may be a plurality of wires. Each of the plurality of wires may reside in a respective cylinder in the sheath outside of the interior space when the self-expanding stent is enclosed in the interior space. Deploying the self-expanding stent may cause each of the plurality of wires to be extracted from the respective cylinder. At least one of the plurality of wires may be a shape-memory wire. The shape-memory wire may be adapted to bend away from a central axis of the self-expanding stent. At least two of the plurality of wires may be connected to each other along at least a partial length of the two wires by a membrane.

The medical appliance may be deployed in a lumen of a human body and the external body may release the bioactive agent.

A medical device is provided that includes a tissue scaffold; a sheath adapted to enclose the tissue scaffold in an interior space during deployment; and an external body comprising endothelial cells attached to the tissue scaffold and adapted to lie outside the interior space of the sheath when the tissue scaffold is enclosed in the sheath.

The external body may be attached to a distal end of the tissue scaffold. The external body may be a membrane. The membrane may be non-porous. The external body may include a bioactive agent. The tissue scaffold may be a porous structure.

BRIEF DESCRIPTION OF THE DRAWINGS

FIGS. 3A-3C are schematic cross-sectional representations of the exemplary embodiment of FIG. 1 with a catheter delivery mechanism showing the self-expanding stent in varying degrees of deployment.

FIG. 8A is a schematic representation of an exemplary embodiment of the present invention utilizing a balloon catheter for deployment of the stent and having wires as the external drug-eluting body.

FIG. 8B is a cross-section of the exemplary embodiment of the present invention shown in FIG. 8A cut along line VIIIB-VIIIB.

FIG. 9A is the exemplary embodiment of the present invention shown in FIG. 8A showing the balloon catheter in an expanded state.

FIG. 9B is a cross-section of the exemplary embodiment of the present invention shown in FIG. 9A cut along line IXB-IXB.

DETAILED DESCRIPTION

Figure 2:
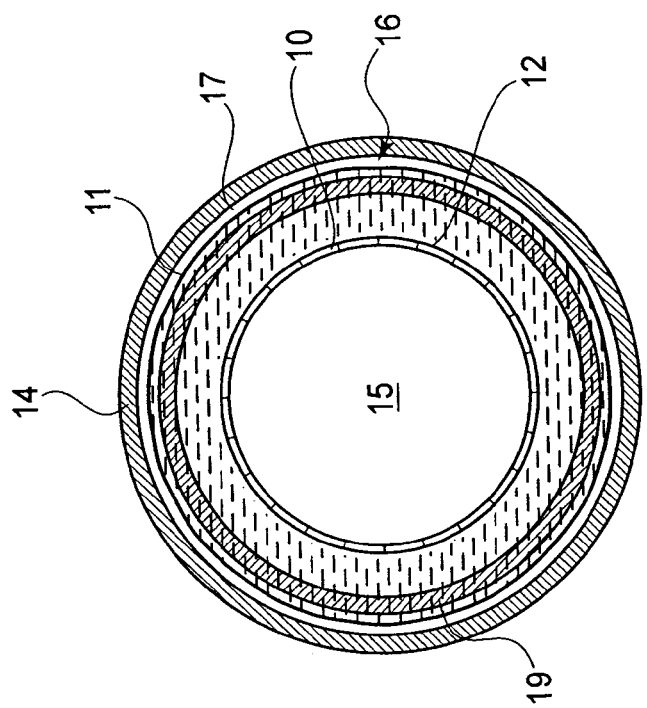
FIG. 2 is an end-on view of the exemplary embodiment of FIG. 1 from the line II-II.

An exemplary embodiment of the present invention separates the drug coating from the SE stent by creating a system in which the drug is put on an additional element which is located either on the outside of the delivery sheath or inside the wall of the delivery sheath.

For example, a standard, bare SE stent may be loaded into a delivery sheath. A membrane or thin tube may be connected on the distal end of the SE stent and may be positioned on the outside of the delivery sheath. As the stent is unloaded out of the sheath, it will expand in the vessel while also expanding, at the same time, the drug membrane that will be located between the stent and the vessel wall. If the stent is pushed out of the delivery tube it will drag along the drug membrane, since the two are connected on the distal end. The drug membrane may experience no sheer force during this deploying operation and in particular no sheer force from the SE stent or the delivery sheath.

Since the drug membrane may be attached to the distal end of the SE stent after the SE stent has been loaded, there may be no sheer force on the drug membrane during the loading operation. An additional advantage may be that coating the drug membrane avoids the problem of coating a complex stent design.

Since the drug may be provided to the membrane without having the large mass of the stent in place, it may be possible to provide a much more accurate drug dose. For instance, a long polymer membrane may be extruded, coated on the outside with a drug, then cut to a required and/or desired length, and then weighed. If the drug dose exceeds the desired amount, an additional piece of membrane may be removed before attaching the membrane to the stent.

The drug membrane may be made either with or without holes to provide blood flow to side-branches. The membrane may be elastic so that it clamps itself to the sheath on the outside.

The delivery sheath may be modified to provide a chamber for the drug-infused membrane. For instance, in the situation of a very soft material being used for the outside drug membrane, a very thin outer protection tube may be added that is connected proximally to the delivery sheath. As the stent is pushed out of the sheath and is dragged along the drug membrane, it will drag the membrane out of its chamber between the delivery sheath and the outer protective element (the outer sheath).

Alternatively, wires may be used instead of a drug membrane. The wires may be coated in a material including a bioactive agent, weighed, and then attached to the distal end of the SE stent. The wires may rest against the outer surface of the delivery sheath or may be banded to the outside of the delivery sheath by a biodegradable and/or releasable band. Alternatively, channels may be extruded in the delivery sheath in which the drug-coated wires that are connected on the distal part to the SE stent may be inserted. This may result in a situation similar to the one described above, but instead of having a membrane in between the vessel wall and the stent, there will be a number of drug-loaded wires (or alternatively, hollow tubes) positioned between the SE stent and the vessel wall. Drug-coated wires provide complete access to the side-branch.

The wires may be longer than the actual stent, so that the drug eluting section of this employed system may extend beyond the SE stent itself. In a further exemplary embodiment, flat memory strips may be used with a shape memory to bend outward on the proximal end. The shape memory strips may comprise Nitinol. In this alternative exemplary embodiment, an SE stent may be positioned in the beginning of a side-branch vessel and have the drug wires (strips) bending out into the main vessel. Alternatively, an SE stent may be positioned in a main branch in the vicinity of a side-branch vessel and the drug wires (strips) may bend into the side-branch vessel.

An alternative exemplary embodiment combines both systems, membrane and wires, by having a number of polymer membrane rings on the outside of the sheath connected along the axis by wires and connected on the distal part to the stent.

An alternative exemplary embodiment utilizes a bucky paper tube (for instance a carbon nanotube or other variation of buckminsterfullerene) and/or a fiber network (for instance, metal, polymer or ceramic fibers) as the reservoir for the bioactive agent and/or as the external drug-eluting body. A fiber network of IrOx fibers may have a catalytic effect in transforming peroxide into oxide and hydrogen. In an alternative exemplary embodiment wire with a catalytic effect and other wires with a drug load (and possibly other wires made out of a highly radiopaque material) may be combined. Likewise, wire and membrane combinations having various properties in various components of the combination may also be possible.

In an alternative exemplary embodiment, magnetic wires may be utilized in conjunction with encapsulation technologies in which magnetic kernels may be surrounded by drugs in micro-capsules. The micro-capsules may be injected in the chamber in the wall of the delivery sheath or in between the delivery sheath and the protective outer sheath. During unloading of the stent from the delivery sheath, the bio-absorbable particles may be dragged along by magnetic forces. The particles may remain magnetically coupled to the magnetic wires and may release their drug-load over time.

Open (meshed) coverings, wires, or closed coverings may be used. Using open drug covered membranes may avoid blocking the bloodstream to side vessels and/or the blood supply to the vessel wall, and therefore may not need to be released fully before the expanding element is released. There may be only one actuating mechanism in the device, which may be a benefit in regards to space and safety. The open drug-releasing outer elements may allow deploying systems that do not block side-access.

Alternative exemplary methods of attaching an outer ePTFE sheath to one side of a self-expanding stent (for instance, a Sentinol stent) are possible. ePTFE may be fused to ePTFE by applying pressure at high temperatures (for example, 395 degrees Celsius).

It may be possible to attach the external body to the stent by using a procedure entailing outside air pressure applied to an assembly where an outer ePTFE covering is mounted on a stent, mounted on an inner covering, and mounted on a mandrel. A possible disadvantage of this method may be that the drug coating has to be applied to the covering after the covering has been attached to the stent, as a drug coating may be destroyed by the high temperatures. Coating the external body prior to attaching it to the stent may have certain benefits, including the ease of calculating the amount of bioactive agent by weighing due to the high ratio of bioactive agent to inert material in the weighing process.

An alternative exemplary embodiment provides a ring or small patches of ePTFE to the stent prior to loading. A separate external body may be coated with drugs over most or all of its surface, and solder-equipment or an infrared laser may be used to spot-weld the drug-coated external body to the ePTFE. The ePTFE may already be mounted to the stent.

Alternative exemplary embodiments may utilize glue to attach the drug-eluting external body to the stent.

The delivery system may be manufactured, by starting with an existing delivery catheter and grinding or laser ablating away the outer layer on the distal end to create a reduced diameter outer sheath. A second extruded thin tube may then be placed around this distal tip of the catheter and welded or glued to the catheter at the proximal side of the reduced diameter outer sheath area. The second extruded thin tube should have an inner diameter greater than the reduced diameter outer sheath area of the catheter in order to provide a gap.

In case of an aneurism, a robust sheath on the stent may be needed to keep the blood flow through the interior of the stent or other medical appliance. Some devices and grafts utilize Nitinol systems with ePTFE and/or polyester coverings. These devices may be loaded into a polymer delivery tube and pushed out during a procedure to close off the aneurism. An exemplary embodiment of the present invention may be used in conjunction with a conventional system for treating an aneurism by adding a drug-loaded external body (sheath or wires) outside of the conventional device.

In an alternative exemplary embodiment, the sheath material may be an electro-active polymer or combination of polymers.

Figure 1:
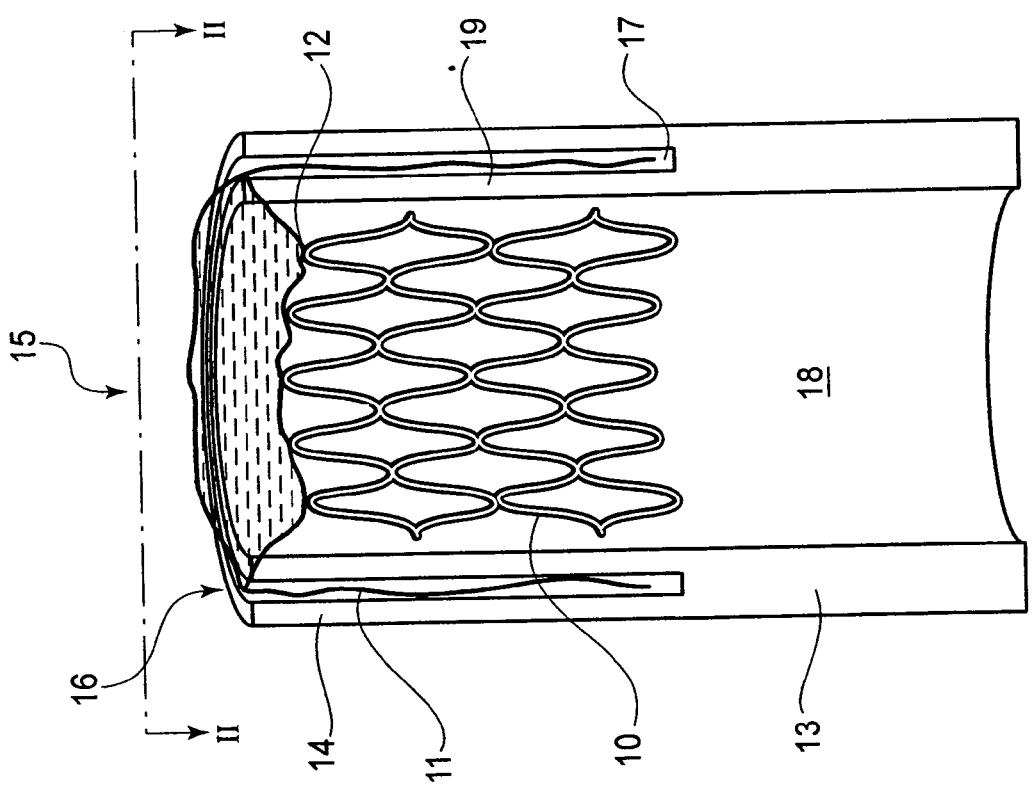
FIG. 1 is a schematic cross-sectional representation of an exemplary embodiment of the present invention showing a self-expanding stent with an external membrane in a delivery sheath.

FIG. 1 is a schematic cross-sectional representation of an exemplary embodiment of the present invention showing self-expanding stent 10 (also referred to herein as SE stent 10) with external membrane 11 in delivery sheath 13. SE stent 10 may extend farther down in delivery sheath 13 than is shown in FIG. 1. External membrane 11 attaches to SE stent 10 at distal end 12 of SE stent 10. Delivery sheath 13 includes outer sheath 14 and inner sheath 19 at the distal end. Outer sheath 14 is flush with a proximal end of delivery sheath 13. Inner sheath 19 defines interior space 18 that encloses SE stent 10 in its predeployed, contracted position. Outer sheath 14 and inner sheath 19 define annular space 17 between them that encloses external membrane 11. Delivery sheath 13 has two openings on a distal end, interior opening 15 accessing interior space 18 enclosing SE stent 10 and annular opening 16 accessing annular space 17 enclosing external membrane 11. External membrane 11 extends out of annular opening 16 and over a distal end of inner sheath 19 to attach to distal end 12 of SE stent 10.

FIG. 2 is an end-on view of the exemplary embodiment of FIG. 1 from the line II-II. The end-on view includes outer sheath 14 on an outer diameter and external membrane 11 in annular space 17 accessed by annular opening 16 on the next inner diameter. External membrane 11 is stretched across the surface of inner sheath 19 on the next inner diameter and SE stent 10 has distal end 12 in interior opening 15 at the most central diameter.

FIGS. 3A-3C are schematic cross-sectional representations of the exemplary embodiment of FIG. 1 with catheter delivery mechanism 31 showing SE stent 10 in varying degrees of deployment. FIG. 3A shows SE stent 10 in a predeployment state in which SE stent 10 is completely enclosed by delivery sheath 13. Catheter delivery mechanism 31 may attach to a catheter, and may attach slideably to delivery sheath 13. Catheter delivery mechanism 31 may occupy interior space 18 of delivery sheath 13 and may include stent abutment 32 adapted to engage SE stent 10. Catheter delivery mechanism 31 may be actuated by an actuator on the catheter to move catheter delivery mechanism 31 with respect to delivery sheath 13.

FIG. 3B shows SE stent 10 in a partially deployed state in which SE stent 10 is partially enclosed by delivery sheath 13 and partially extending out of delivery sheath 13. Partial actuation of catheter delivery mechanism 31 moves catheter delivery mechanism 31 with respect to delivery sheath 13. In some exemplary embodiments, delivery sheath 13 moves in the direction of arrow 33, while catheter delivery mechanism 31 remains stationary. The relative motion of catheter delivery mechanism 31 and delivery sheath 13 causes stent abutment 32 to press against the proximal side of SE stent 10, causing SE stent 10 to be ejected from delivery sheath 13. SE stent 10 expands when ejected from delivery sheath 13, and may expand to press against the inner wall of the lumen in which the deployment is performed. External membrane 11, which is attached to SE stent 10 at a distal end, is drawn out of annular space 17 and may be sandwiched between SE stent 10 and the inner wall of the lumen by the expansion force of SE stent 10.

FIG. 3C shows SE stent 10 in another partially deployed state in which SE stent 10 is nearly completely deployed and substantially extending out of delivery sheath 13. Continuing actuation of catheter delivery mechanism 31 will cause the proximal side of SE stent 10 to be ejected from delivery sheath 13. Further actuation of catheter delivery mechanism 31 will fully deploy SE stent 10 and will allow the removal of the catheter, catheter delivery mechanism 31, and delivery sheath 13.

Figure 4:
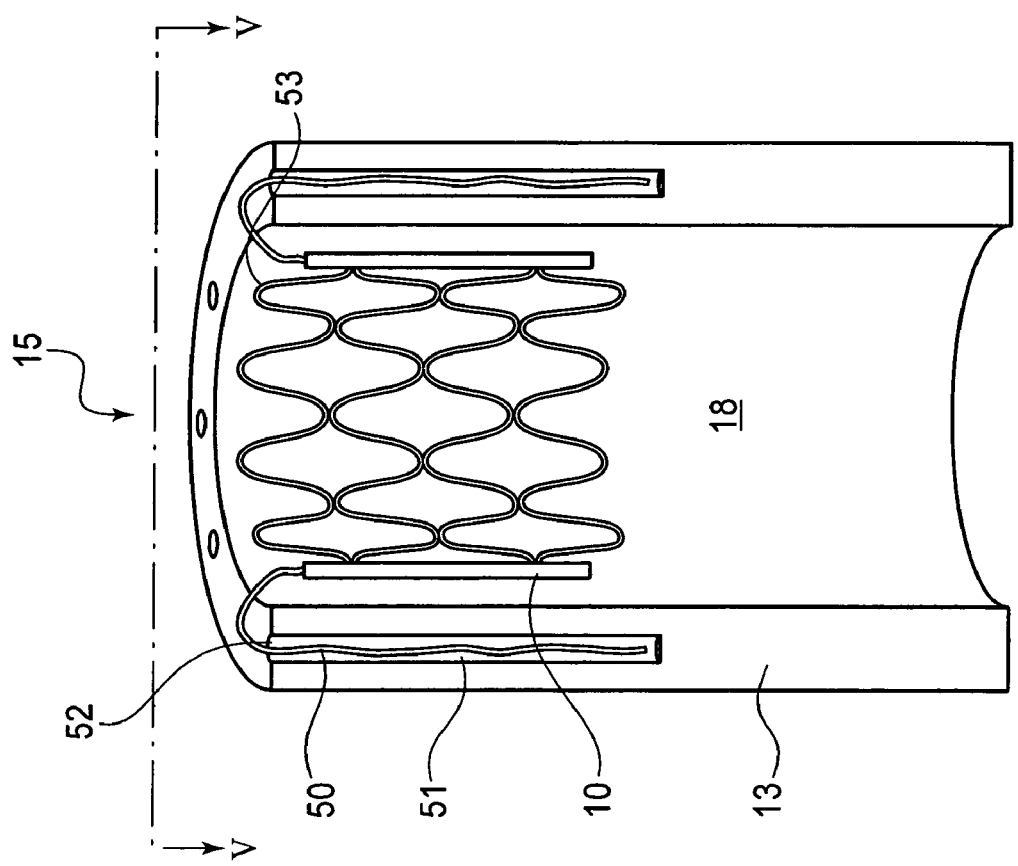
FIG. 4 is a schematic cross-sectional representation of an exemplary embodiment of the present invention showing a self-expanding stent with an external set of wires in a delivery sheath.

FIG. 4 is a schematic cross-sectional representation of an exemplary embodiment of the present invention showing SE stent 10 with external wires 50 in delivery sheath 13. SE stent 10 may extend farther down in delivery sheath 13. Any number of external wires 50 may be attached to SE stent 10 at distal end 53 of SE stent 10. Delivery sheath 13 includes wire holes 51 at the distal end. The number of wire holes 51 may be the same as the number of external wires 50. Interior space 18 of delivery sheath 13 encloses SE stent 10 in its predeployed, contracted position. Wire holes 51 enclose external wires 50. Delivery sheath 13 has openings on a distal end, interior opening 15 accessing interior space 18 enclosing SE stent 10 and wire hole openings 52 accessing wire holes 51 enclosing external wires 50. External wires 50 extend out of wire holes 51 and over a distal end of delivery sheath 13 to attach to distal end 53 of SE stent 10.

Figure 5:
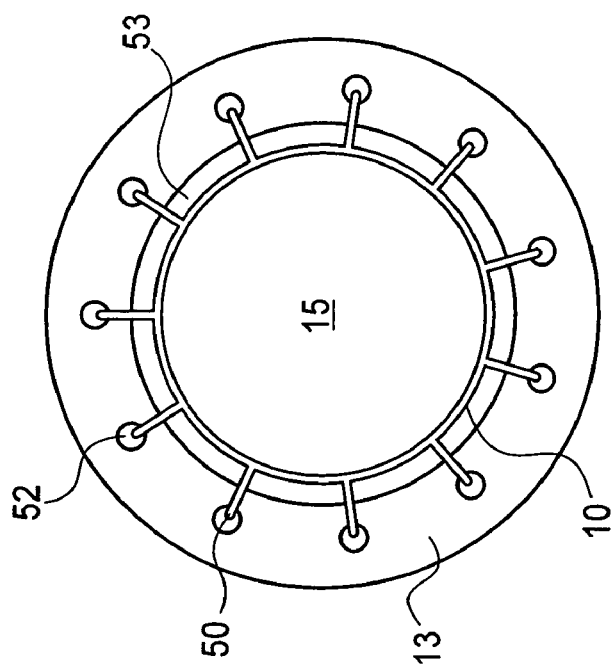
FIG. 5 is an end-on view of the exemplary embodiment of FIG. 4 from the line V-V.

FIG. 5 is an end-on view of the exemplary embodiment of FIG. 4 from the line V-V. The end-on view includes delivery sheath 13 including wire hole openings 52. External wires 50 stretch across the surface of delivery sheath 13 and attach SE stent 10 at distal end 12 in interior opening 15 at the most central diameter.

Figure 6:
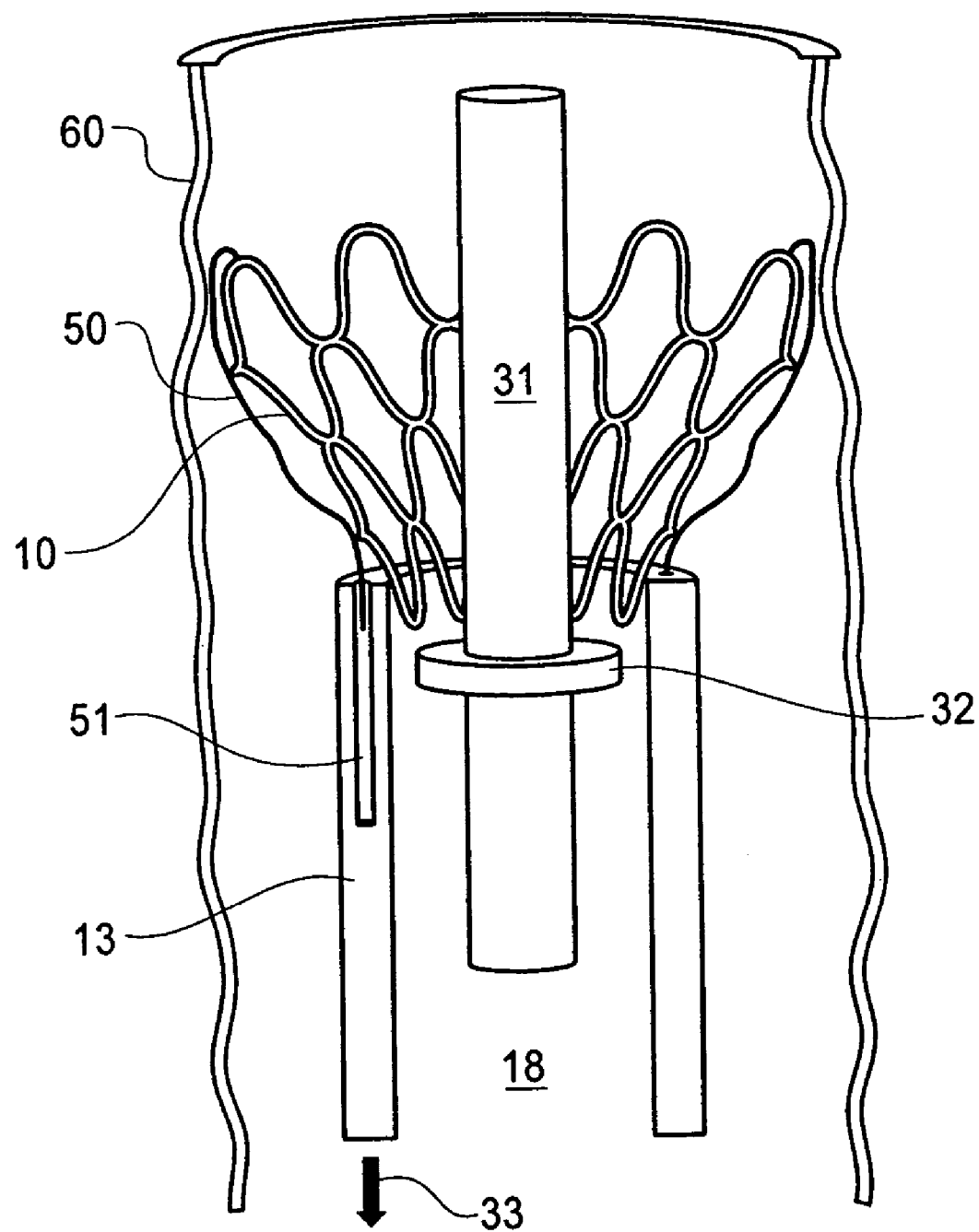
FIG. 6 is a schematic cross-sectional representation of the exemplary embodiment of FIG. 4 with a catheter delivery mechanism showing the self-expanding stent in a partially deployed state.

FIG. 6 is a schematic cross-sectional representation of the exemplary embodiment of FIG. 4 with catheter delivery mechanism 31 showing SE stent 10 in a partially deployed state in which SE stent 10 is nearly completely deployed and substantially extending out of delivery sheath 13. Catheter delivery mechanism 31 may attach to a catheter, and may attach slideably to delivery sheath 13. In some exemplary embodiments, delivery sheath 13 moves in the direction of arrow 33, while catheter delivery mechanism 31 remains stationary. Catheter delivery mechanism 31 may occupy interior space 18 of delivery sheath 13 and may include stent abutment 32 adapted to engage SE stent 10. Catheter delivery mechanism 31 may be actuated by an actuator on the catheter to move catheter delivery mechanism 31 with respect to delivery sheath 13. Partial actuation of catheter delivery mechanism 31 moves catheter delivery mechanism 31 with respect to delivery sheath 13. The relative motion of catheter delivery mechanism 31 and delivery sheath 13 causes stent abutment 32 to press against the proximal side of SE stent 10, causing SE stent 10 to be ejected from delivery sheath 13. SE stent 10 expands when ejected from delivery sheath 13, and may expand to press against inner wall 60 of the lumen in which the deployment is performed. External wires 50, which are attached to SE stent 10 at a distal end, are drawn out of wire holes 51 and may be sandwiched between SE stent 10 and inner wall 60 of the lumen by the expansion force of SE stent 10. Continuing actuation of catheter delivery mechanism 31 will cause the proximal side of SE stent 10 to be ejected from delivery sheath 13. Further actuation of catheter delivery mechanism 31 will fully deploy SE stent 10 and will allow the removal of the catheter, catheter delivery mechanism 31, and delivery sheath 13.

FIGS. 7A-7D are schematic representations showing an exemplary method for manufacturing an exemplary embodiment of the present invention. SE stent 10 is constructed of any appropriate material, including stainless steel or plastic, and is contracted into a constricted state. External membrane 11 may be ePTFE (expanded polytetrafluoroethylene), a fibrous material, or any other appropriate material. External membrane 11 may be continuous or may have holes and/or slits of any appropriate size and/or shape. External membrane 11 may be impregnated with a bioactive agent by soaking, spraying or any other appropriate method. The amount of bioactive agent in external membrane 11 may be determined by weighing, for instance weighing prior to coating with a bioactive agent and weighing after coating with the bioactive agent. External membrane 11 may include attachment area 70, which may be adapted to attach to SE stent 10. Attachment area 70 may be the same material as external membrane 11 or may be a different material. Attachment area 70 may attach to SE stent 10 by a spot welding process, a pressure treatment, a combination heat/temperature process, or by any other appropriate method. The attachment process used to attach external membrane 11 to SE stent 10 may be isolated to attachment area 70 to avoid damaging the bioactive agent in external membrane 11 or may be designed to not damage the bioactive agent.

Figure 7A:
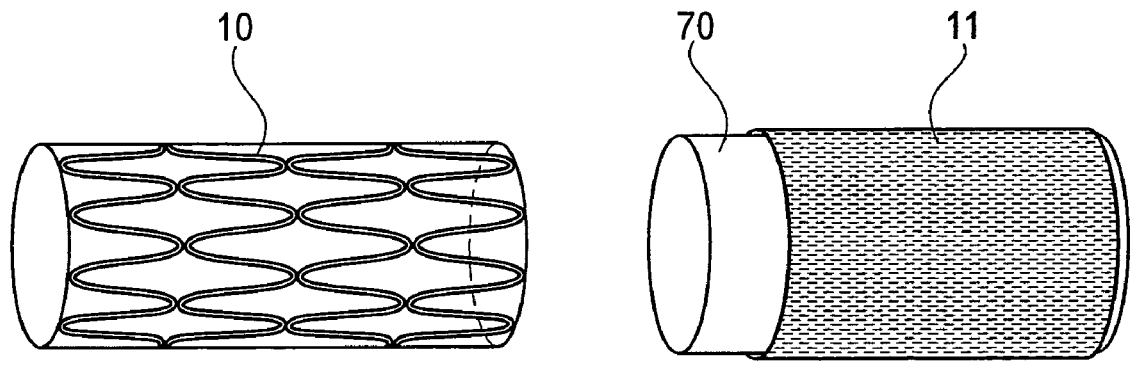
FIGS. 7A-7D are schematic representations showing an exemplary method for manufacturing an exemplary embodiment of the present invention.
Figure 7B:
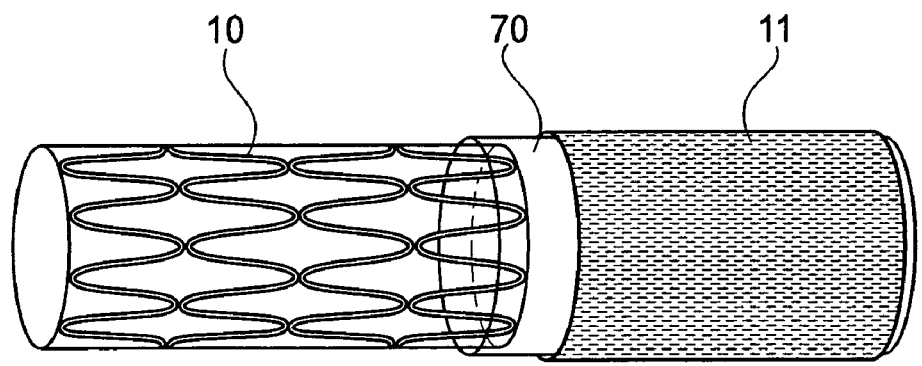
Figure 7C:
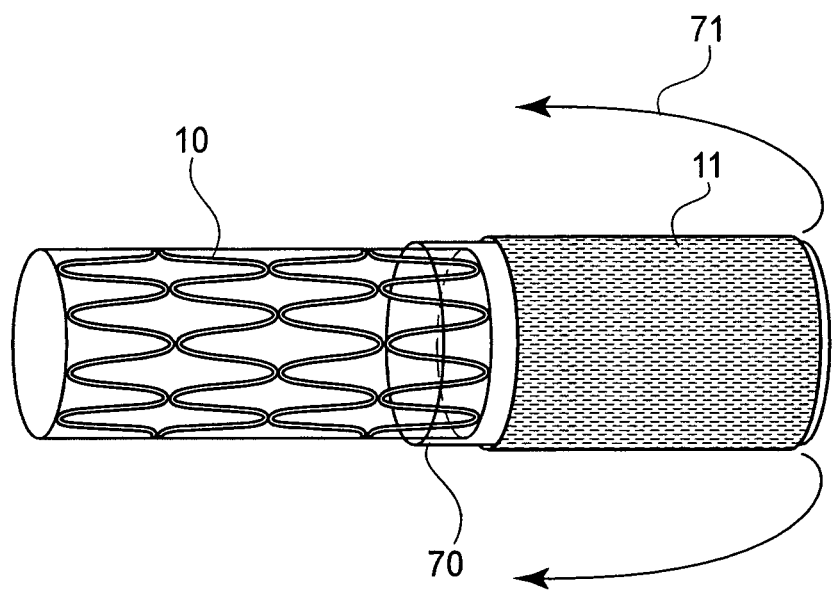
Figure 7D:
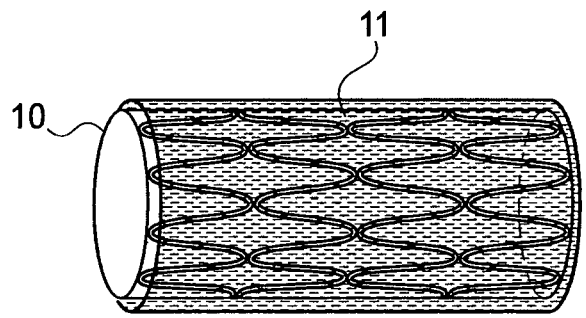
Figure 7E:
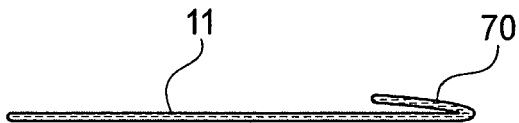
FIG. 7E is a cross-section of the exemplary embodiment of the membrane shown in FIG. 7D.

FIG. 7A shows SE stent 10 and external membrane 11 having attachment area 70 in a separated condition. FIG. 7B shows attachment area 70 of external membrane 11 overlapping a distal region of SE stent 10. Attachment area 70 may be attached to the distal area of SE stent 10 by any appropriate method. FIG. 7C includes arrows 71 illustrating the direction that external membrane 11 may be flipped with respect to SE stent 10 to complete the production of the SE stent 10 including external membrane 11. FIG. 7D shows the completed SE stent including external membrane 11 along the outside of external membrane 11. FIG. 7E shows a cross section of external membrane 11 in a completed production state (as in FIG. 7D), showing external membrane 11 doubled back over attachment area 70.

FIG. 8A is a schematic representation of an exemplary embodiment of the present invention utilizing balloon catheter 80 for deployment of stent 81 and having wrapped external wires 84 as an external drug-eluting body. FIG. 8A shows stent 81 in a predeployed state on balloon catheter 80 on catheter 82. Wrapped external wires 84 attach to stent 81 at attachment points 85 on distal end of stent 81 then wrap around stent 81 in a helical fashion toward the proximal end of stent 81. Wrapped external wires 84 terminate in wire holder 83 mounted on catheter 82 proximal from stent 81.

FIG. 8B is a cross-section of the exemplary embodiment of the present invention shown in FIG. 8A cut along line VIIIB-VIIIB. FIG. 8B shows stent 81 in a predeployed state on balloon catheter 80. Wrapped external wires 84 attach to stent 81 at attachment points 85 and wrap around stent 81.

FIG. 9A is the exemplary embodiment of the present invention shown in FIG. 8A showing balloon catheter 80 expanded for deployment of stent 81 and having wrapped external wires 84 as an external drug-eluting body. FIG. 9A shows stent 81 in a partially deployed state on balloon catheter 80 on catheter 82. Wrapped external wires 84 attach to stent 81 at attachment points 85 on distal end of stent 81 then wrap around stent 81 in a helical fashion toward the proximal end of stent 81. Wrapped external wires 84 have been pulled loose from wire holder 83 by the expansion of balloon catheter 80.

FIG. 9B is a cross-section of the exemplary embodiment of the present invention shown in FIG. 9A cut along line IXB-IXB. FIG. 9B shows stent 81 in a partially deployed state on balloon catheter 80. Wrapped external wires 84 attach to stent 81 at attachment points 85 and wrap around stent 81.

Figure 10:
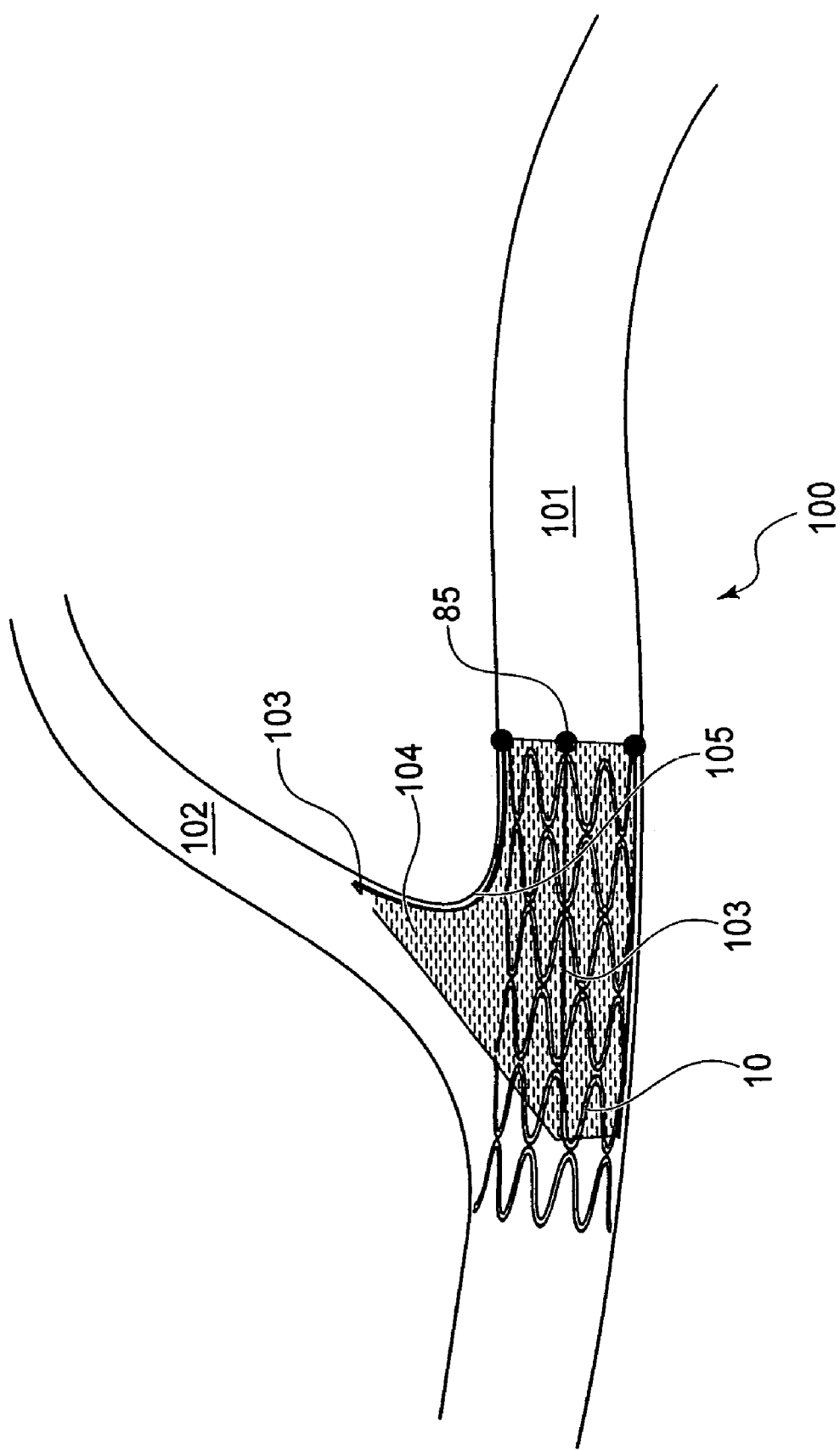
FIG. 10 is a schematic representation of an exemplary embodiment of the present invention showing a stent having shape-memory wires and a membrane as the drug-eluting external body in a deployed state in a branched lumen.

FIG. 10 is a schematic representation of an exemplary embodiment of the present invention showing stent 10 having shape-memory wires 103 and membrane 104 as the drug-eluting external body in a deployed state in branched lumen 100. Branched lumen 100 includes main branch 101 and side branch 102. Shape-memory wires 103 attach to stent 10 at attachment points 85. Stent 10 is deployed in main branch 101 in the region of side branch 102. Shape-memory wire 103 closest to side branch 102 bends around apex 105 of branched lumen 100. Membrane 104 is connected to shape-memory wires 103 or is situated external to shape-memory wires 103. Membrane 104 is stretched by shape-memory wires 103 that is situated in side branch 102.

A method of producing the medical device may include attaching an external body to a stent and coupling the stent to a delivery arrangement. The external body may include a bioactive agent. The external body may include a membrane and the method may include spot welding the membrane to the stent and inverting the membrane after attaching the membrane to the stent. The inverting operation may include moving a portion of the membrane opposite a point of attachment towards the point of attachment and further moving the portion of the membrane opposite the point of attachment to an exterior of the stent and towards a section of the stent distal to the point of attachment.

The stent may include a self-expanding stent and the delivery arrangement may include a delivery sheath for the self-expanding stent. The coupling operation may include inserting the self-expanding stent into the delivery sheath in a contracted state. The coupling operation may include situating the membrane on an exterior of the delivery sheath. The coupling operation may include situating the membrane in an annular space of the delivery sheath. The annular space may be situated in between a central space and an exterior of the delivery sheath.

The external body may include a plurality of wires. The stent may include a self-expanding stent. The delivery arrangement may include a delivery sheath for the self-expanding stent. The coupling operation may include inserting the self-expanding stent into the delivery sheath in a contracted state.

The coupling operation may include situating the plurality of wires on an exterior of the delivery sheath. The coupling operation may include situating each of the plurality of wires in a chamber in the delivery sheath. Each of the chambers may be situated in between a central space and an exterior of the delivery sheath. The plurality of wires may include a plurality of shape-memory wires. The delivery arrangement may include a balloon catheter.

Figure 11:
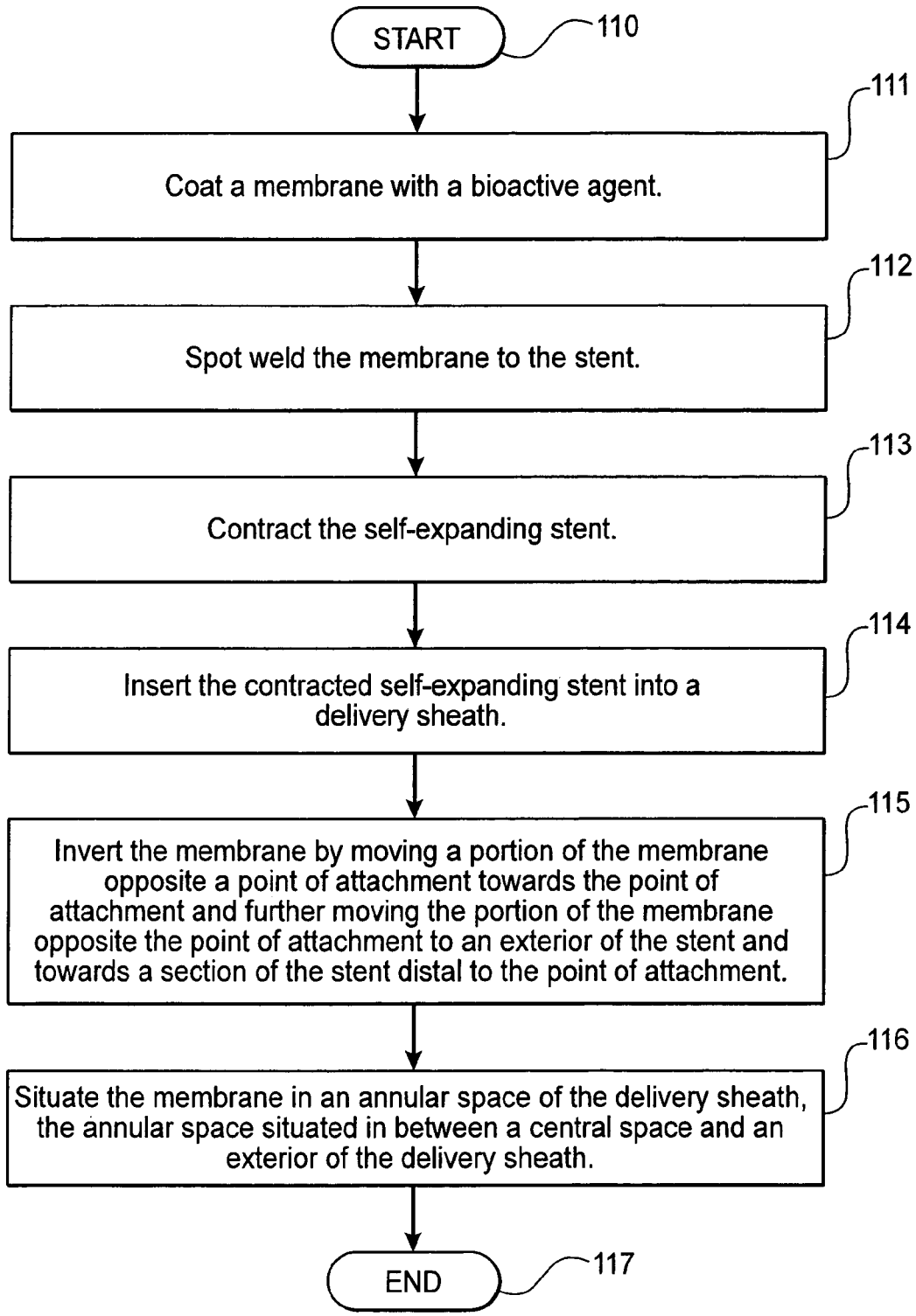
FIG. 11 is a flow chart illustrating an exemplary method for manufacturing an exemplary embodiment of the present invention.

FIG. 11 is a flow chart illustrating an exemplary method for manufacturing an exemplary embodiment of the present invention. The flow in FIG. 11 starts in start circle 110 progresses to action 111, which indicates to coat a membrane with a bioactive agent. From action 111 the flow proceeds to action 112, which indicates to spot weld the membrane to the stent. From action 112 the flow proceeds to action 113, which indicates to contract the self-expanding stent. From action 113 the flow proceeds to action 114, which indicates to insert the contracted self-expanding stent into a delivery sheath. From action 114 the flow proceeds to action 115, which indicates to invert the membrane by moving a portion of the membrane opposite a point of attachment towards the point of attachment and further moving the portion of the membrane opposite the point of attachment to an exterior of the stent and towards a section of the stent distal to the point of attachment. From action 115 the flow proceeds to action 116, which indicates to situate the membrane in an annular space of the delivery sheath, the annular space situated in between a central space and an exterior of the delivery sheath. Alternatively, the membrane may be inverted over an inner tube of the delivery sheath to be arranged external to the delivery sheath. The annular space may be created by mounting an outer tube over the inverted membrane. The outer tube may be glued or welded to the catheter (see FIGS. 12A to 12C). From action 116 the flow proceeds to end circle 117.

Figure 12A:
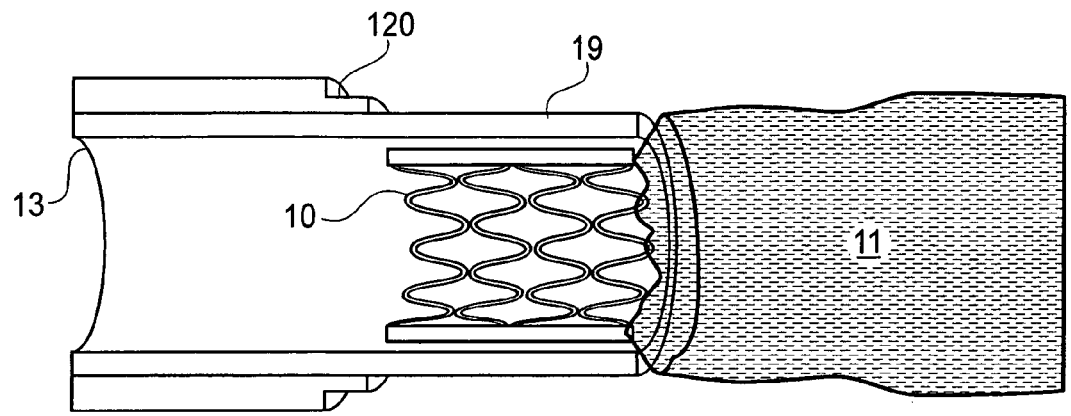
FIGS. 12A-12C are schematic cross-sectional representations showing an alternative exemplary method for manufacturing an exemplary embodiment of the present invention.

FIG. 12A shows a schematic representation showing an alternative exemplary method for manufacturing an exemplary embodiment of the present invention. FIG. 12A shows SE stent 10 in delivery sheath 13. External membrane 11 is attached to SE stent 10 and extends away from delivery sheath 13. Delivery sheath 13 includes inner sheath 19 at the distal end and step 120 at a transition between inner sheath 19 of delivery sheath 13 and the main body of delivery sheath 13.

Figure 12B:
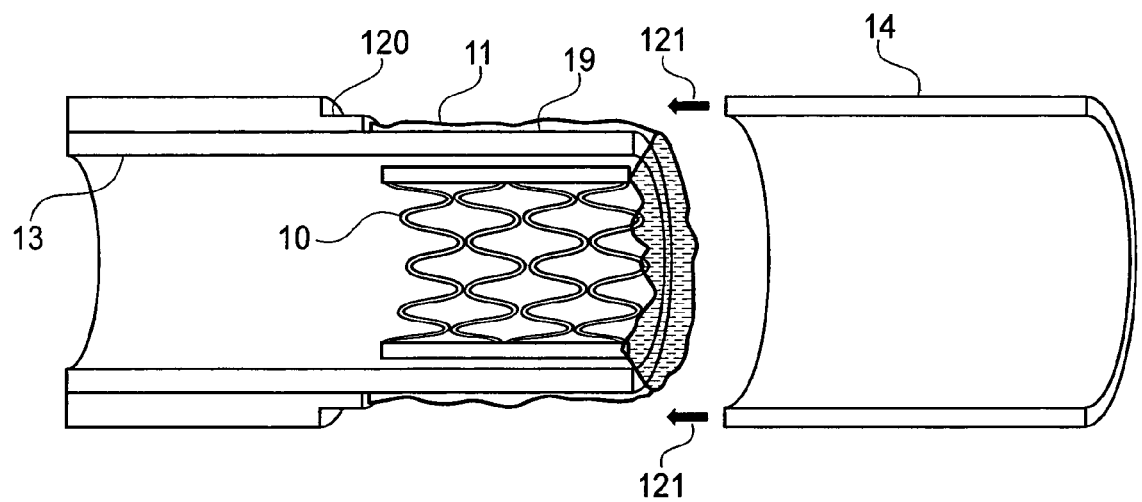

FIG. 12B shows external membrane 11 inverted over inner sheath 19 and attached to SE stent 10. External membrane 11 extends over inner sheath 19 to the vicinity of step 120, though alternatively step 120 may be distant from inverted external membrane 11. Outer sheath 14 is shown separated from delivery sheath 13. Arrows 121 show the direction of movement that outer sheath 14 is moved to attach to delivery sheath 13.

Figure 12C:
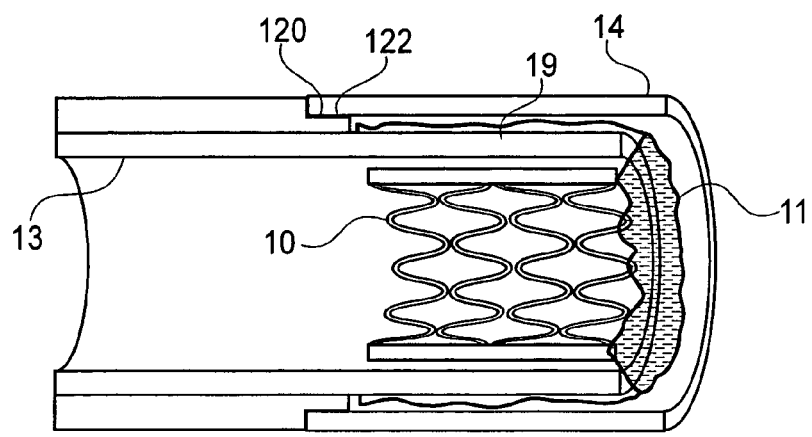

FIG. 12C shows outer sheath 14 positioned over external membrane 11 and inner sheath 19. Outer sheath 14 may form a friction fit with delivery sheath 13 via step 120 interacting with friction area 122 of outer sheath 14. Alternatively, outer sheath 14 may be welded, glued or attached by any other appropriate method to delivery sheath 13. FIG. 12C shows SE stent 10 including external membrane 11 in delivery sheath 13 and ready to be deployed.

As used herein, the term "therapeutic agent" includes one or more "therapeutic agents" or "drugs". The terms "therapeutic agents", "active substance" and "drugs" are used interchangeably herein and include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethyl ketone); antiproliferative agents such as enoxaparin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; antineoplastic/antiproliferative/antimitotic agents such as paclitaxel, epothilone, cladribine, 5-fluorouracil, methotrexate, doxorubicin, daunorubicin, cyclosporine, cisplatin, vinblastine, vincristine, endostatin, trapidil, halofuginone, and angiostatin; anticancer agents such as antisense inhibitors of c-myc oncogene; antimicrobial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamicin, rifampin, minocycline, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anticoagulants such as D-Phe-Pro-Arg chloromethyl ketone, an RGD peptide-containing compound, heparin, antithrombin compounds, platelet receptor antagonists, antithrombin antibodies, antiplatelet receptor antibodies, enoxaparin, hirudin, warfarin sodium, dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1") and bone morphogenic proteins ("BMPs"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of antirestenosis agents include p15, p16, p18, p19, p21, p27p53, p57Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds that have a molecular weight of less than 100 kD.

Exemplary cells include stem cells, progenitor cells, endothelial cells, adult cardiomyocytes, and smooth muscle cells. Cells can be of human origin (autologous or allogeneic) or from an animal source (xenogeneic), or genetically engineered. Non-limiting examples of cells include side population (SP) cells, lineage negative (Lin–) cells including Lin–CD34–, Lin–CD34+, Lin–c Kit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, GII cells endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tert-block copolymers (SIBS); polyvinylpyrrolidone, including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and copolymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, spray coating using an ultrasonic nozzle, and polyelectrolyte coating (layer by layer).

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

While the present invention has been described in connection with the foregoing representative embodiment, it should be readily apparent to those of ordinary skill in the art that the representative embodiment is exemplary in nature and is not to be construed as limiting the scope of protection for the invention as set forth in the appended claims.

What is claimed is:

1. A medical appliance, comprising:
a self-expanding stent;
a sheath comprising an external surface, an internal surface, a length, and an annular channel situated between the external surface and the internal surface, the internal surface bounding an interior space, the sheath adapted to enclose the self-expanding stent in the interior space of the sheath; and an external body comprising a bioactive agent attached to the self expanding stent and adapted to lie within the annular channel when the self-expanding stent is enclosed in the sheath.

2. The medical appliance of claim 1, wherein the external body is attached to a distal end of the self-expanding stent.

3. The medical appliance of claim 2, wherein the external body is a membrane.

4. The medical appliance of claim 3, wherein the membrane is impermeable to a fluid.

5. The medical appliance of claim 4, wherein the bioactive agent comprises endothelial cells.

6. The medical appliance of claim 3, wherein the membrane is porous to a fluid.

7. The medical appliance of claim 2, wherein the external body is a plurality of wires.

8. The medical appliance of claim 7, wherein each of the plurality of wires resides in a respective cylinder in the annular channel of the sheath when the self-expanding stent is enclosed in the interior space.

9. The medical appliance of claim 8, wherein deploying the self expanding stent causes each of the plurality of wires to be extracted from the respective cylinder.

10. The medical appliance of claim 7, wherein at least one of the plurality of wires is a shape-memory wire.

11. The medical appliance of claim 10, wherein the shape-memory wire is adapted to bend away from a central axis of the self-expanding stent.

12. The medical appliance of claim 7, wherein at least two of the plurality of wires are connected to each other along at least a partial length of the two wires by a membrane.

13. The medical appliance of claim 1, wherein deploying the self-expanding stent causes the membrane to be extracted from the annular channel.

14. The medical appliance of claim 1, wherein:
the medical appliance is deployed in a lumen of a human body; and
the external body releases the bioactive agent.

15. The medical appliance of claim 1, wherein the annular channel has a length that is less than the length of the sheath.

16. A medical device, comprising:

a tissue scaffold comprising a proximal end and a distal end;

a sheath comprising an external surface and an internal surface, the internal surface bounding an interior space, the sheath adapted to enclose the tissue scaffold in the interior space; and an external body comprising a proximal end and a distal end, the external body comprising a bioactive agent, the distal end of the external body being attached to the distal end of the tissue scaffold, the external body adapted to lie outside the interior space when the tissue scaffold is enclosed in the sheath; and means for simultaneously expanding the tissue scaffold and the external body by first expanding the distal ends of the tissue scaffold and the external body and thereafter expanding the proximal ends of the tissue scaffold and the external body.

17. The medical device of claim 16, wherein the external body is a membrane.

18. The medical device of claim 16, wherein the external body further comprises a bioactive agent.

19. The medical device of claim 16, wherein the tissue scaffold is a porous structure.

20. The medical device of claim 16, wherein the tissue scaffold is a self-expanding stent.

21. The medical device of claim 16, wherein the bioactive agent comprises endothelial cells.

22. A method of deploying a medical device in a body lumen comprising: providing a medical device comprising:
a self-expanding stent,
a sheath comprising an external surface, an internal surface, a length and an annular channel situated between the external surface and the internal surface, the internal surface bounding an interior space, the sheath adapted to enclose the self-expanding stent in the interior space of the sheath, and
an external body comprising a bioactive agent attached to the self-expanding stent and adapted to lie within the annular channel when the self-expanding stent is enclosed in the sheath; and simultaneously deploying the self-expanding stent and the external body in a body lumen.

* * * * *